US00PP28679P2

(12) United States Plant Patent
Hansen

(10) Patent No.: US PP28,679 P2
(45) Date of Patent: Nov. 21, 2017

(54) ***PHLOX* PLANT NAMED 'FASHIONABLY EARLY CRYSTAL'**

(50) Latin Name: ***Phlox* hybrid**
Varietal Denomination: Fashionably Early Crystal

(71) Applicant: Hans A. Hansen, Zeeland, MI (US)

(72) Inventor: Hans A. Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 0 days.

(21) Appl. No.: 15/530,082

(22) Filed: Dec. 1, 2016

(51) Int. Cl.
*A01H 5/02* (2006.01)

(52) U.S. Cl.
USPC ..... Plt./320

(58) Field of Classification Search
USPC ..... Plt./320
CPC ..... A01H 5/02
See application file for complete search history.

*Primary Examiner* — Kent L Bell

(57) ABSTRACT

A new and unique cultivar of garden *phlox* named *Phlox* 'Fashionably Early Crystal' multi-stemmed, compact, slowly-spreading habit with bright-green, glossy, lanceolate leaves. Flowers are sweetly-fragrant, producing sweetly-fragrant, initially very light lavender-pink flower faces becoming white with light purple eye zones beginning the second week of June, continuing for about five weeks and repeating through mid-fall. Foliage stays clean and resists mildew.

1 Drawing Sheet

Botanical classification: *Phlox* hybrid.
Variety denomination: 'Fashionably Early Crystal'.

BACKGROUND OF THE INVENTION

The present invention relates to a new and distinct cultivar of *Phlox* plant, known as *Phlox* 'Fashionably Early Crystal' and will be referred to hereafter by its cultivar name, 'Fashionably Early Crystal', or the "new plant". The new plant was the result of a single seedling selection from the cross of *Phlox maculata* 'Alpha' (not patented) times *Phlox* 'Amethyst Pearl' U.S. Plant patent application Ser. No. 15/330,047 performed at a wholesale perennial nursery in Zeeland, Mich. on Jun. 13, 2012. The new plant was originally given the breeder code 12-11-04. 'Fashionably Early Crystal' has been asexually propagated by stem cuttings in the greenhouses at the same nursery in Zeeland, Mich. The unique characteristics of the new plant have been found to be reproducible and stable in successive generations of asexually propagated plants and the resultant plants have been found to be identical to the original selection.

No plants of *Phlox* 'Fashionably Early Crystal' have been sold, in this country or anywhere in the world, prior to the filing of this application, nor has any disclosure of the new plant been made prior to the filing of this application with the exception of that which may have been disclosed within one year of the filing date of this application and was either derived directly or indirectly from the inventor.

BRIEF SUMMARY OF THE PLANT

*Phlox* 'Fashionably Early Crystal' is unique from its parents and all other tall garden *phlox* or other *Phlox* known to the inventor. The new plant differs from the female parent *Phlox maculata* 'Alpha' by having white flowers with a tiny light purple eye and broader flower heads. Compared to the male parent 'Amethyst Pearl' the new plant is earlier flowering, producing larger white flowers with a tiny light purple eye on taller plants. Compared to 'Fashionably Princess', co-pending U.S. Plant patent application Ser. No. 15/530,083, the new plant begins flowering about one week later. Further, the new plant differs in flower color. Compared to 'Fashionably Early Flamingo', co-pending U.S. Plant patent application Ser. No. 15/530,085, the new plant differs primarily in flower color. 'Fashionably Early Crystal' differs from all other *phlox* known to the inventor in the following repeatedly observed traits in combination:

1. Plants of compact habit, slowly spreading by short rhizomes, producing clean, glossy, bright-green, lanceolate leaves.
2. Foliage thinker substance than *Phlox paniculata* types showing exceptional powdery mildew resistance.
3. Multiple stems produce rounded heads of flowers very early in the season.
4. Sweetly fragrant flowers on strong flexible stems of about 70 to 80 cm tall producing sweetly-fragrant, initially very light lavender-pink flower faces becoming white with light purple eye zones.
5. Excellent re-blooming through mid-fall when deadheaded.

BRIEF DESCRIPTION OF THE DRAWINGS

The photographs of the new plant demonstrate the unique traits of 'Fashionably Early Crystal' and the overall appearance of the plant at two-years old. The colors are as accurate as reasonably possible with color reproductions. Variation in ambient light spectrum, source and direction may cause the appearance of minor variation in color.

DETAILED BOTANICAL DESCRIPTION

Figure 1:
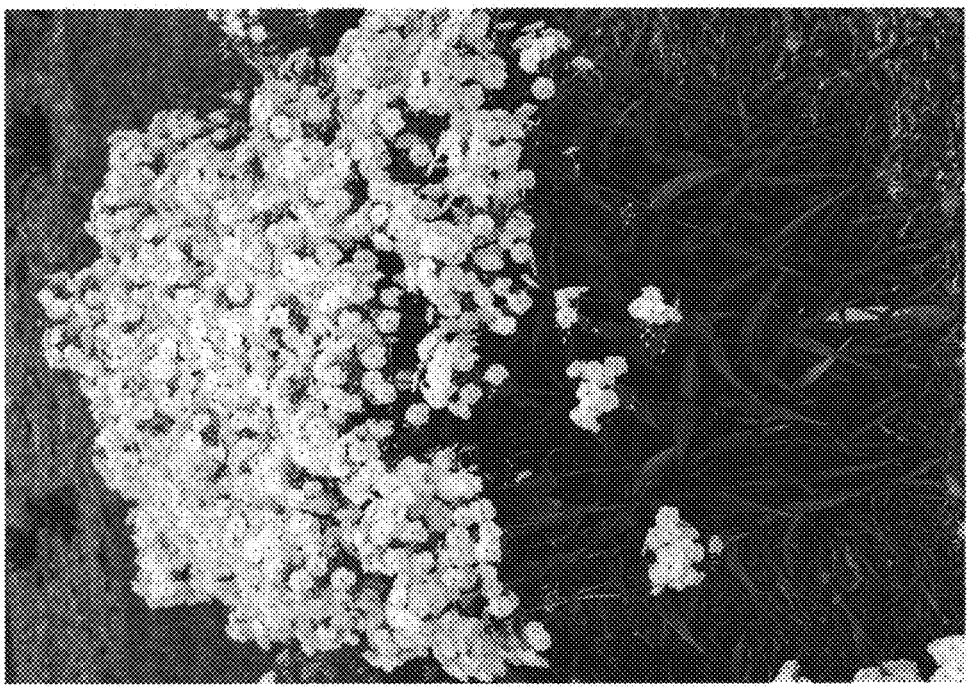
FIG. 1 shows a close-up of the floriferous flower head with flowers and buds.
Figure 2:
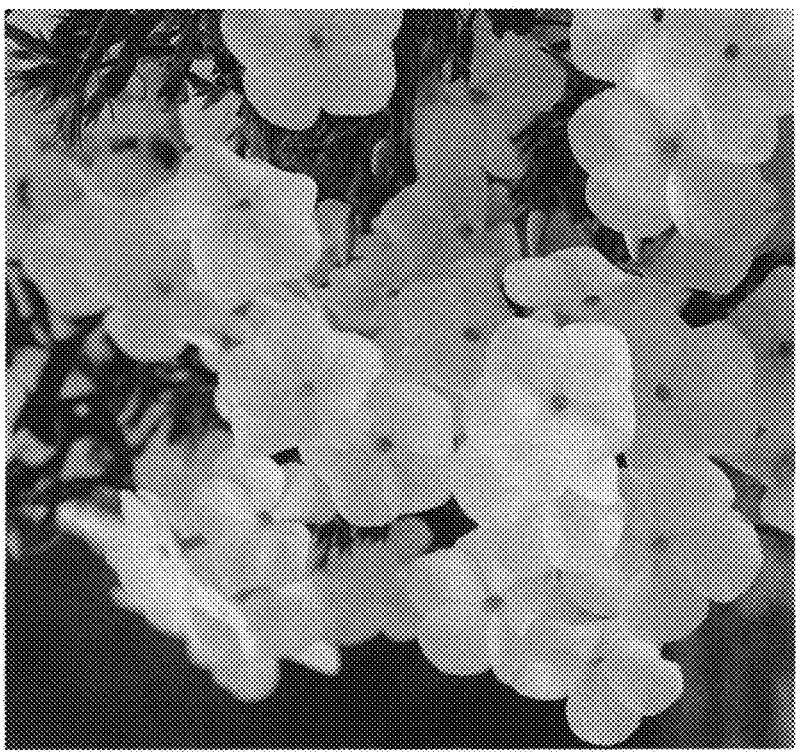
FIG. 2 shows the new plant in flower in the landscape with late spring to early summer foliage.

The following descriptions and color references are based on the 2001 edition of The Royal Horticultural Society Colour Chart except where common dictionary terms are used. *Phlox* 'Fashionably Early Crystal' has not been observed under all possible environments. The phenotype may vary slightly with different growing environments such as temperature, light, fertility, soil pH, moisture and maturity levels, but without any change in the genotype. The following observations and size descriptions are based on two-year-old plants in the full sun trial garden of a wholesale perennial nursery in Zeeland, Mich. with supplemental fertilizer and water as needed.

Botanical classification: *Phlox* hybrid.

Parentage: Female or seed parent *Phlox maculata* 'Alpha' (not patented); male or pollen parent *Phlox* 'Amethyst Pearl' U.S. Plant patent application Ser. No. 15/330,047.

Plant habit: Hardy herbaceous perennial, densely upright, producing about 30 rigid upright stems; about 70 to 80 cm tall at flowering and about 78.0 cm wide at flowers; rounded panicle cluster about 9.0 cm across and 10.0 cm tall; flowering begins about the second week of June in Michigan and continuing for about 5 weeks and repeating through summer and until heavy frost if deadheaded.

Propagation: Stem cuttings; rooting in about 14 days.

Time to produce finished crop in 3.8 liter pots: About 8 to 10 weeks; moderate rate of growth.

Root: Primary roots to about 1.0 mm thick; secondary fibrous and freely branching; color creamy white to tan depending on soil type.

Leaves: Simple, opposite, lanceolate, entire; glabrous abaxial; puberulent adaxial; lustrous adaxial, matte abaxial; acute apex, rounded base; to about 10.0 cm long by about 2.1 cm wide, average about 8.8 cm long by about 1.5 cm wide.

Leaf color at flowering: Abaxial between RHS 138B and RHS 138A; adaxial nearest 137A.

Foliage fragrance: None detected.

Veins: Pinnate; glabrous abaxial, slightly puberulent adaxial; mid-vein about 1.0 mm wide at base, slightly sunken adaxial and raised abaxial.

Vein color: Abaxial midrib between RHS 144B and RHS 144A, adaxial midrib between RHS 76B and RHS 76C; other adaxial and abaxial veins not noticeable.

Petiole: Leaves sessile.

Stems: Terete; stiff; strong; upright; glabrous to minutely puberulent; average about 75.0 cm long and 3.5 mm diameter at base.

Stem color: Nearest N144C with speckling of between RHS 187B and RHS 187C.

Nodes: About 10 per stem below flowers; average internode length about 6.5 cm; shorter proximally and longer distally.

Node color: Between RHS 145A and RHS 145B.

Flowers: Perfect; salverform, typically with five petals; about 3.2 cm long total with tube about 2.8 cm long; face about 3.0 cm across; held in a branched compound corymb of about 55 to 70 flowers; attitude upright to outward.

Flower longevity: About 5 days on plant or as cut flower; self-cleaning.

Flower fragrance: Pleasantly sweet.

Buds one to two days prior to opening: Narrowly oblanceolate, to nearly clavate; acute apex with petals twisted about each other; about 2.1 cm long and 2.5 mm diameter in tube and swollen to 4.0 mm diameter toward apex.

Bud color: Tube base nearest 145C, distal tube between RHS 77B and RHS 77C; swollen apex nearest RHS 76D.

Petals: Five, glabrous except pubescent for about 4.0 mm to 6.5 mm from base of adaxial tube; margin entire; apex rounded; basal 2.8 cm fused into tube, to a diameter of about 3.0 diameter; adaxial about 10.0 mm of tube throat, rounded limbs with rounded to emarginate apex; limbs about 1.4 cm across, imbricate about 3.0 mm of the petals to either side.

Petal color: Abaxial tube base nearest RHS 155D, abaxial tube middle nearest RHS 76A, abaxial middle and distal face near white, lighter than RHS 155D with very light blush of nearest 76D; adaxial tube base nearest RHS 155D, middle tube between RHS 76B and RHS 76C with pubescent hairs the same, near throat nearest RHS 75A, adaxial face perimeter near white, lighter than RHS 155D with very light blush of nearest RHS 76D fading with age to white, lighter than RHS 155D, near throat nearest RHS 75A gradually lightening toward apex.

Androecium:

*Filaments*.—Usually five, fused to inner petals except free in terminal 1.0 mm; varying lengths between 15.0 mm and 20.0 mm above base, less than 0.2 mm in diameter; white, lighter than RHS 155D.

*Anther*.—Five; oblong elliptic; dorsifixed; longitudinal; about 2.0 mm long by 0.5 mm wide; color nearest RHS 13B.

*Pollen*.—Nearly microscopic, spherical; color nearest RHS 17B.

Gynoecium: One pistil per flower.

*Style*.—Terete; about 2.7 cm long and 0.3 mm diameter when flower is mature; nearest RHS 145C.

*Stigma*.—Trifurcate in the distal 2 mm, less than 0.25 mm in diameter; persistent after flower abscission; nearest RHS 2C.

*Ovary*.—Superior; elliptic, about 2.0 mm long and 1.0 mm diameter; color nearest RHS N144A.

Sepals: Five, glabrous; lanceolate; sharply acute apex, margin entire; individually about 9.0 mm long and 1.0 mm wide; fused in basal 6.5 mm forming tube 2.5 mm diameter at base and 4.0 mm diameter at apex.

Sepal color: Abaxial apex nearest RHS 187A, midsection nearest RHS 138B with tinting of nearest RHS 187B, margins (about 0.5 mm wide) translucent with some pigment nearest RHS 187D; adaxial apex nearest RHS 187A, midsection nearest RHS 138B with slight tinting of nearest RHS 187B and margins translucent with some pigment nearest RHS 187D.

Peduncle: Minutely puberulent, stiff, strong, upright, terete; about 2.0 mm diameter at base of main stem and 1.0 mm diameter of branches; flowering portion about 8.0 cm long with flowers spreading 10.0 cm across the inflorescence.

Peduncle color: Nearest RHS N144C with speckling between RHS 187B and RHS 187C.

Fruit: Dehiscent capsule with flat base and acute to mucronate apex; about 7.0 mm long and 5.0 mm diameter; color at maturity nearest RHS 161C.

Seeds: Up to four; slightly flattened ellipsoid; about 3.5 mm long and 2.5 mm across and 2.0 mm thick; color nearest RHS 202A.

Hardiness and culture: The new plant grows best with plenty of moisture and adequate drainage; hardy to at least from USDA zone 4 through 8.

Disease and pest resistance: *Phlox* 'Fashionably Early Crystal' demonstrated the excellent powdery mildew resistance under conditions that would normally show symptoms.

It is claimed:

1. A new and distinct cultivar of hybrid *phlox* plant named *Phlox* 'Fashionably Early Crystal', as herein described and illustrated, especially suitable as a potted plant, for the garden, for attracting hummingbirds and butterflies, and for cut flower arrangements.

* * * * *